United States Patent
Keller

Patent Number: 6,136,004
Date of Patent: Oct. 24, 2000

[54] SURGICAL NAIL FORCEPS

[75] Inventor: Arnold Keller, Kayhude, Germany

[73] Assignee: Waldemar Lin (GmbH & Co.), Hamburg, Germany

[21] Appl. No.: 09/310,224

[22] Filed: May 12, 1999

[30] Foreign Application Priority Data

May 13, 1998 [EP] European Pat. Off. ............. 98108893

[51] Int. Cl.⁷ .................................................. A61B 17/58
[52] U.S. Cl. ............................................................ 606/104
[58] Field of Search ................................. 606/205, 206, 606/207, 208, 209, 210, 211, 104, 100; 254/18–25, 26 R, 26 E; 433/150, 159, 151; 81/418, 426.5

[56] References Cited

U.S. PATENT DOCUMENTS

| | | | |
|---|---|---|---|
| 3,236,275 | 2/1966 | Smith | 145/50 |
| 4,385,628 | 5/1983 | Straith | 606/84 |
| 4,911,154 | 3/1990 | Vickers | 606/104 |
| 5,496,341 | 3/1996 | Sauer et al. | 606/167 |
| 5,562,447 | 10/1996 | Moy et al. | 433/150 |
| 5,984,272 | 11/1999 | Crider | 254/18 |

FOREIGN PATENT DOCUMENTS

| | | |
|---|---|---|
| 2 668 919 | 5/1992 | France . |
| 2 743 490 | 7/1997 | France . |
| 372 842 | 11/1993 | Germany . |
| 687 122 A5 | 9/1996 | Germany . |

*Primary Examiner*—Michael Buiz
*Assistant Examiner*—Tan-Uyen T. Ho
*Attorney, Agent, or Firm*—Morrison & Foerster LLP

[57] ABSTRACT

In surgical nail forceps with two members (2, 7) connected to one another in an articulated manner, at least one of the members is designed as an impaction tool, this member being designed to transmit impact forces to the nail (20).

8 Claims, 1 Drawing Sheet

SURGICAL NAIL FORCEPS

The invention relates to surgical nail forceps.

To drive surgical nails in using a striking tool, for example a hammer, impaction instruments are known which hold the nails firmly and secure against loss (FR-A-26 68 919, AT-B-372842). To remove the nails, public prior use documents disclose extraction forceps which correspond to conventional gripping forceps in terms of construction and function. In surgical applications, the use of a large number of different tools is disadvantageous from the point of view of ease of handling. The greater the number of tools used, the greater the space they take up and the greater the work involved in preparing and cleaning them. Moreover, the need to change between tools in the rapid succession of driving the nails in and extracting them is unfavourable, and disadvantageous when, for example, a nail has to be extracted and then put back in place.

The object of the invention is to provide surgical forceps in which the stated disadvantages are minimized.

The solution according to the invention lies in the features of claim 1, preferably also in those of the subclaims. Accordingly, in medical nail forceps with two members connected to one another in an articulated manner, at least one of the members is designed as an impaction tool which has, in addition to a curved grip part, a straight strengthening element. The result of this is that the member designed as the impaction tool (hereinafter: impaction member) is, despite the ergonomically curved shape of the grip, designed to transmit the impact forces to the nail. The advantage of this is that one and the same tool is available for driving in and extracting the nails and a change of tool is not necessary. Deviations from the straight-line configuration can be compensated with reference to the articulation between the forceps members.

A generically different arrangement for fixing by means of clips is known which has, as the holding instrument, a chisel-like impaction rod with a pivot lever which is arranged so as to pivot thereon. The clip is held in a trough-like recess on the pointed side of the impaction rod and is clamped securely by a jaw-like projection of the pivot lever. A disadvantage of the known arrangement is that, on the one hand, a second instrument is required for complete impaction of the clip since this cannot be brought about by the impaction rod because of the jaw-like projection engaging between clip and bone surface, and, on the other hand, the impaction rod is not suitable for extraction since it cannot grip the clip when the latter has been fully impacted, and its straight grip permits transmission of only small tensile forces.

The strengthening element can (but does not have to) be designed in one piece with the grip of the impaction member. To ensure that the impact forces can be transmitted reliably to the nail, the impaction member is expediently provided with a guide, for example a bore, which receives the rear end of the nail. This does not mean that the other member could not also be involved in securing the nail in the forceps as this is being driven in. However, the less this is necessary, the better, so that the operating surgeon does not need to pay so much attention to how the forceps is being held. The guide also permits easier extraction since experience shows that a nail is easier to loosen by applying pivot torques and lateral forces in addition to tensile forces. The guide is expediently designed as a bore in the jaw part of the impaction member. The rear end face of the bore lying opposite the opening is designed in such a way that it cooperates with the rear end face of the nail in order to transmit the impaction forces. A strike surface is expediently arranged at the rear end of the impaction member. The rear end is to be understood as that end of the grip remote from the jaw. The strike surface used for driving the nail in is designed as the reverse end of a strike head. The strike head can also have a front hammer blow surface which can be used for extracting a nail.

To hold the nail in the guide of the impaction member, use is expediently made of the other forceps member, which is therefore also referred to hereinafter as the holding member. If the guide for the rear end of the nail is designed as a bore, it advantageously has a lateral opening, i.e. an opening situated transverse to its longitudinal axis, which opening faces towards the holding member and through which a retaining projection arranged on the holding member can engage in order to exert a holding action on the nail when the forceps is closed. This can be effected by non-positive engagement, although it is more advantageous for the projection to cooperate with the nail with a positive engagement. For this purpose, it is expedient if the nail has, in its rear shank area, a recess cooperating with the retaining projection.

According to a further advantageous feature of the invention, the forceps has pulling grips, i.e. grip parts arranged transverse to the direction of extraction. To apply the tensile force needed for extraction, it is irrelevant whether the pulling grips are arranged nearer the front or nearer the rear of the forceps grip; however, it is expedient for them to be arranged in the front area of the grips so that the surgeon can grip them with his fingers during extraction and at the same time can place the palm of his hand round the forceps grip.

The nail forceps according to the invention is explained in detail hereinbelow with reference to the drawing which illustrates an advantageous illustrative embodiment. In the drawing.

Figure 1:
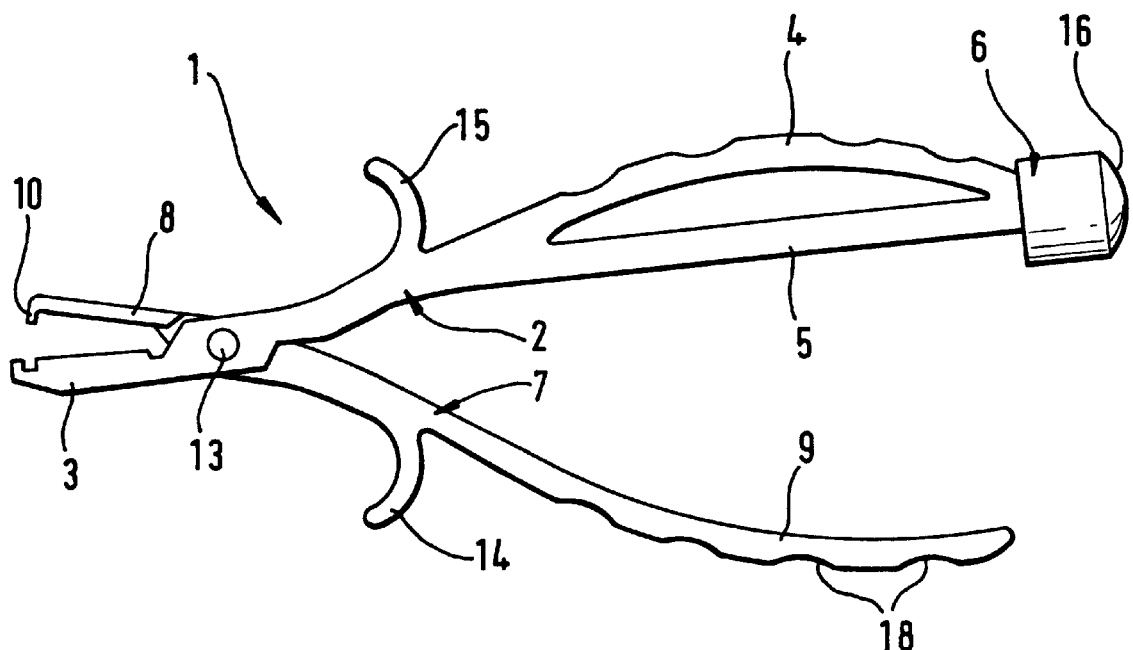
FIG. 1 shows the nail forceps in an opened position.
Figure 2:
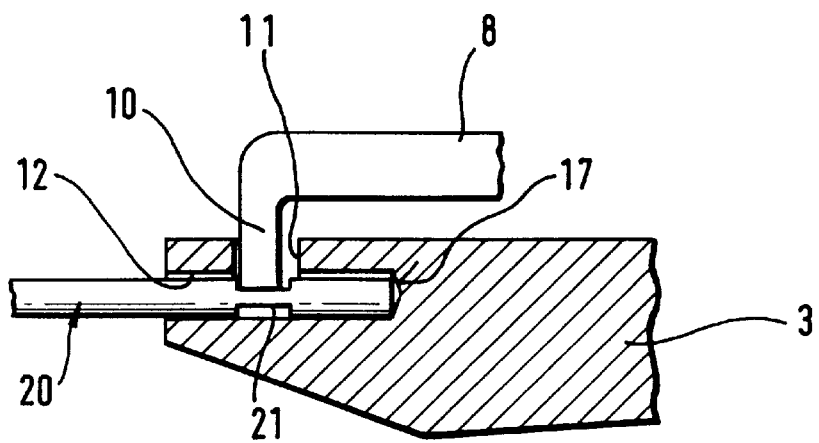
FIG. 2 shows a longitudinal section through the jaw of the forceps, with a nail inserted, in an enlarged representation.

The surgical nail forceps 1 consists of two members 2, 7 which are connected to one another via a pivot hinge 13 and which each have a grip 4, 9 and a jaw part 3, 8. It is preferably made of a corrosion-resistant material, such as stainless steel.

The forceps member 2, which forms the impaction member, has in its jaw part 3 a longitudinally arranged bore 12 for receiving the rear end of the nail 20. Its diameter is chosen in such a way as to provide a clearance fit with the nail 20. The bore 12 extends as a blind hole over a length which is sufficient for securely guiding the nail 20, for example a length of the order of one centimetre. It has a lateral opening 11 facing the other jaw part 8. Arranged at the front end of the jaw part 8 there is a retaining projection 10 which engages in the opening 11 when the forceps is closed. The opening 11 may be, but does not have to be, considerably larger than the retaining projection 10. It is important that the retaining projection 10 cooperates with the nail 20 via the opening 11 so that the nail 20 is clamped securely when the forceps 1 is closed. To ensure a positive engagement during extraction, a recess 21 is arranged on the nail 20 in such a way that the retaining projection 10 can engage in the recess 21. The end face 17 of the bore 12 generally serves to transmit the impact forces to the nail 20.

The grips 4, 9 are of an ergonomically curved shape. On their outer sides they are provided with a number of grip dimples 18. Provided at the rear end of the grip 4 of the impaction member 2 there is a strike head 6 having a strike surface 16 which has a pronounced crown shape and which is aligned transverse to the axis of the bore 12. The axis of the bore 12 is aligned with the strike surface.

A strengthening element 5 is provided in the manner of a chord on the grip 4 and its rear end is arranged approximately centrally on that side of the strike head 6 facing away from the strike surface 16, and its front end is connected integrally with the grip 4 near the hinge 13. The strengthening element 5 is of rectilinear design and is sufficiently strong to transmit all practically occurring impact forces safely and without buckling. It runs almost in alignment with the bore 12. Its deviation from the straight is intended, in the illustrated example, to create sufficient space between the forceps grips for the surgeon'ss hand. Likewise, the course of the strengthening element and of the parts of the impaction member adjoining the jaw end is substantially perpendicular, so that the impaction member deviates only slightly from the line of action of the impact force and there is no danger of its deflecting to the side under the effect of the impact.

In the area of the grips 4, 9 near the hinge, two curved pulling grips 14, 15 are arranged opposite one another. They lie in the plane defined by the grips 4, 9 and each point approximately perpendicularly away from the latter. They are each intended for receiving a finger during extraction of nails. The location at which the pulling grips 14, 15 are arranged is chosen such that if, for example, they are gripped by the index finger and middle finger of one hand, the grips 4, 5 come to lie in the palm of the hand. In this way, high tensile forces can be applied with reliable guiding of the forceps, and rotaty and pivoting movements' can additionally be exerted.

What is claimed is:

1. Surgical nail forceps, comprising two members, wherein at least one of said members is an impaction member comprising a curved hand grip part and a straight strengthening element.

2. The surgical nail forceps according to claim 1, wherein the impaction member has a jaw part comprising a longitudinal guide for the rear end of a nail.

3. The surgical nail forceps according to claim 1 or 2, wherein the impaction member 1 comprises a strike surface at its rear end.

4. The surgical nail forceps according to claim 1 or 2, wherein the strengthening element forms one piece with the impaction member.

5. The surgical nail forceps according to claim 2, wherein the guide on said impaction member comprises a bore having a rear end face formed in the bore that serves as a limit stop.

6. The surgical nail forceps according to claim 5, wherein the bore on the impaction member comprises a lateral opening, and another of said members of said forceps comprises a retaining projection which engages in the lateral opening.

7. The surgical nail forceps according to claim 1, further comprising pulling grips.

8. An arrangement comprising the forceps according to claim 6 and a nail which comprises a recess near its rear end, configured so that when the nail is inserted into the bore as far as the limit stop, the lateral opening and the retaining projection cooperate with the recess of said nail in order to secure said nail.

* * * * *

UNITED STATES PATENT AND TRADEMARK OFFICE

CERTIFICATE OF CORRECTION

PATENT NO. : 6,136,004

ISSUED : October 24, 2000

INVENTOR(S) : Arnold Keller

It is certified that error appears in the above-identified patent and that said Letters Patent is hereby corrected as shown below:

In [73] Assignee:

"Waldemar Lin (GmbH & Co.)" should be --Waldemar Link (GmbH & Co.)--

Signed and Sealed this

Twenty-second Day of May, 2001

*Attest:*

NICHOLAS P. GODICI

*Attesting Officer*     *Acting Director of the United States Patent and Trademark Office*